US008657733B2

(12) United States Patent
Ayre et al.

(10) Patent No.: US 8,657,733 B2
(45) Date of Patent: *Feb. 25, 2014

(54) CONTROL SYSTEMS FOR ROTARY BLOOD PUMPS

(75) Inventors: Peter Joseph Ayre, Crows Nest (AU); Lee Thomas Glanzmann, Darlington (AU); Nicholas Oliver Von Huben, Bexley North (AU)

(73) Assignee: Thoratec Corporation, Pleasanton, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 12/468,951

(22) Filed: May 20, 2009

(65) Prior Publication Data

US 2011/0015465 A1    Jan. 20, 2011

Related U.S. Application Data

(63) Continuation of application No. 11/592,354, filed on Nov. 3, 2006, now abandoned.

(30) Foreign Application Priority Data

Nov. 4, 2005   (AU) .............................. 2005906123

(51) Int. Cl.
    *A61N 1/00*   (2006.01)
(52) U.S. Cl.
    USPC .......................................................... 600/17
(58) Field of Classification Search
    USPC .................................................. 600/16–18
    See application file for complete search history.

(56) References Cited

U.S. PATENT DOCUMENTS

| 4,296,500 A | 10/1981 | Monties et al. |
| 4,611,578 A | 9/1986 | Heimes |
| 4,957,504 A | 9/1990 | Chardack |
| 4,969,864 A | 11/1990 | Schwarzmann et al. |

(Continued)

FOREIGN PATENT DOCUMENTS

| EP | 1 354 606 | 10/2003 |
| WO | WO 01/05023 | 1/2001 |

(Continued)

OTHER PUBLICATIONS

Ayre et al., "Identifying physiologically significant pumping states in implantable rotary blood pumps using non-invasive system observers", Proc. of $25^{th}$ Annual Inter. Conf. of IEEE, pp. 439-442 (2003).

(Continued)

*Primary Examiner* — Scott Getzow
(74) *Attorney, Agent, or Firm* — Squire Sanders (US) LLP

(57) ABSTRACT

The present invention generally relates to a control system for a rotary blood pump adapted to move blood in a patient. The control system comprises a means for measuring and varying the speed of the pump and a means for measuring the pulsatility index of a patient, and the control system is adapted to maintain the pulsatility index at or near a predetermined value by varying the speed of the pump. The pulsatility index is derived from the amplitude of the actual pump speed over a predetermined time period. Optionally, also, the control system can calculate the second derivative of instantaneous speed of the rotary blood pump and use the calculation of the second derivative of instantaneous speed to detect a suction event, and help prevent it.

20 Claims, 4 Drawing Sheets

(56) References Cited

U.S. PATENT DOCUMENTS

| | | | |
|---|---|---|---|
| 5,220,259 | A | 6/1993 | Werner et al. |
| 5,289,821 | A | 3/1994 | Schwartz |
| 5,728,069 | A | 3/1998 | Montevecchi et al. |
| 5,888,242 | A | 3/1999 | Antaki et al. |
| 6,027,498 | A | 2/2000 | Mutch et al. |
| 6,066,086 | A | 5/2000 | Antaki et al. |
| 6,068,588 | A | 5/2000 | Goldowsky |
| 6,071,093 | A | 6/2000 | Hart |
| 6,183,412 | B1 | 2/2001 | Benkowski et al. |
| 6,227,797 | B1 | 5/2001 | Watterson et al. |
| 6,277,078 | B1 | 8/2001 | Porat et al. |
| 6,395,026 | B1 | 5/2002 | Aboul-Hosn et al. |
| 6,443,983 | B1 | 9/2002 | Nagyszalanczy et al. |
| 6,547,753 | B1 | 4/2003 | Plunkett et al. |
| 6,572,530 | B1 | 6/2003 | Araki et al. |
| 6,595,762 | B2 | 7/2003 | Khanwilkar et al. |
| 6,610,004 | B2 | 8/2003 | Viole et al. |
| 6,623,420 | B2 | 9/2003 | Reich et al. |
| 6,685,621 | B2 | 2/2004 | Bolling et al. |
| 6,709,382 | B1 | 3/2004 | Horner |
| 6,752,602 | B2 | 6/2004 | Schulte Eistrup et al. |
| 6,783,328 | B2 | 8/2004 | Lucke et al. |
| 6,866,625 | B1 | 3/2005 | Ayre et al. |
| 6,949,066 | B2 | 9/2005 | Bearnson et al. |
| 6,991,595 | B2 | 1/2006 | Burke et al. |
| 7,138,776 | B1 | 11/2006 | Gauthier et al. |
| 7,141,943 | B2 | 11/2006 | Song et al. |
| 7,494,459 | B2 | 2/2009 | Anstadt et al. |
| 7,645,225 | B2 | 1/2010 | Medvedev et al. |
| 8,096,935 | B2 * | 1/2012 | Sutton et al. .......... 600/16 |
| 2001/0009645 | A1 | 7/2001 | Noda |
| 2002/0183628 | A1 | 12/2002 | Reich et al. |
| 2003/0045772 | A1 | 3/2003 | Reich et al. |
| 2003/0092961 | A1 | 5/2003 | Korakianitis et al. |
| 2003/0199727 | A1 | 10/2003 | Burke et al. |
| 2004/0047736 | A1 | 3/2004 | Nose et al. |
| 2004/0152944 | A1 | 8/2004 | Medvedev et al. |
| 2005/0208095 | A1 | 9/2005 | Hunter et al. |
| 2005/0215843 | A1 | 9/2005 | Medvedev |
| 2006/0149331 | A1 | 7/2006 | Mann et al. |
| 2010/0222632 | A1 | 9/2010 | Poirier |
| 2010/0222633 | A1 | 9/2010 | Poirier |
| 2010/0222634 | A1 | 9/2010 | Poirier |
| 2010/0222635 | A1 | 9/2010 | Poirier |
| 2010/0222878 | A1 | 9/2010 | Poirier |

FOREIGN PATENT DOCUMENTS

| | | |
|---|---|---|
| WO | 01/72352 A2 | 10/2001 |
| WO | WO 01/72352 | 10/2001 |
| WO | WO 03/057280 | 7/2003 |
| WO | 2004/028593 A1 | 4/2004 |
| WO | WO 2004/028593 | 4/2004 |
| WO | 2005/051838 A2 | 6/2005 |
| WO | WO 2005/051838 | 6/2005 |

OTHER PUBLICATIONS

Office Action for U.S. Appl. No. 12/942,908, mailing date May 6, 2011, 12 pgs.

Response to Office Action for U.S. Appl. No. 12/942,908, mailing date Aug. 8, 2011, 6 pgs.

* cited by examiner

CONTROL SYSTEMS FOR ROTARY BLOOD PUMPS

TECHNICAL FIELD

The present invention relates to improvements to control systems for a rotary blood pump.

BACKGROUND ART

To treat cardiac insufficiency or failure, heart assist devices have been used to assist the heart of a patient. These heart assist devices include various pumping devices. A high level of success has been attributed to a particular group of heart assist devices called rotary blood pumps.

In the past, the rotary blood pumps have used control systems which set the pumping speed at a constant rate. This constant rate would not change for the physiological demands of the patient. Therefore, if a patient was exercising the physiological demands for increased blood supply would not be offset by a matched increased pumping rate or speed of the rotary blood pump.

Therefore, there is a need for a control system that allows a rotary blood pump to match the physiological needs of a patient.

Rotary blood pumps also usually provide a continuous flow which is additionally pulsed by the residual function of the patient's heart. Rotary blood pumps operating at predetermined fixed pumping rate often tend to over-pump or under-pump blood from the ventricle depending on the physiological needs of the patient and this may lead to deleterious effects on the patient including, but not limited to, suction events or ventricular collapse. Suction events occur where the pressure within a ventricle is less than the intrathoracic pressure around the heart. The net result is a partial or complete collapse of the ventricle.

The present invention aims to or at least address or ameliorate one or more of the disadvantages associated with the above mentioned prior art, or to provide a useful alternative.

DISCLOSURE OF THE INVENTION

In accordance with a first aspect, the present invention consists of a control system for a rotary blood pump adapted to move blood in a patient, the control system comprising a means for measuring and varying the speed of the pump and a means for measuring the pulsatility index of a patient, the control system adapted to maintain the pulsatility index at or near a predetermined value by varying the speed of the pump, and the pulsatility index is derived from the amplitude of the actual pump speed over a predetermined time period.

Preferably, the predetermined time period is about 40 milliseconds. Preferably, the predetermined value is between 20 to 45 units.

Preferably, the control system calculates the second derivative of instantaneous speed of the rotary blood pump and uses the calculation of the second derivative of instantaneous speed detect a suction event.

Preferably, the control system determines imminence of a suction event based on the stroke work. Preferably, the target speed is pulsed in cooperation with the heart. Preferably, the control system includes a selective mode that minimises target pump speed to achieve forward blood flow through both the pump and aortic valve, whilst avoiding retrograde flow. Preferably, the selective mode sets target speed at about 1250 rpm.

Preferably, the control system calculates or detects left ventricular pressure with respect to time. Preferably, the control system uses the pulsatility index to derive preload. Preferably, the control system maintains the preload within a predetermined range by adjusting target speed. Preferably, the control system mimics starling curve responses of a natural heart. Preferably, the control system uses preload to mimic starling curve responses of a natural heart.

In accordance with a second aspect, the present invention consists of a control system for use with rotary blood pumps, wherein the control system includes a selective mode that minimises target pump speed to achieve forward blood flow through both the pump and aortic valve, whilst avoiding retrograde flow.

BRIEF DESCRIPTION OF DRAWINGS

Embodiments of the present invention will now be described with reference to the accompanying drawings wherein.

BEST MODES FOR CARRYING OUT THE INVENTION

Figure 1:
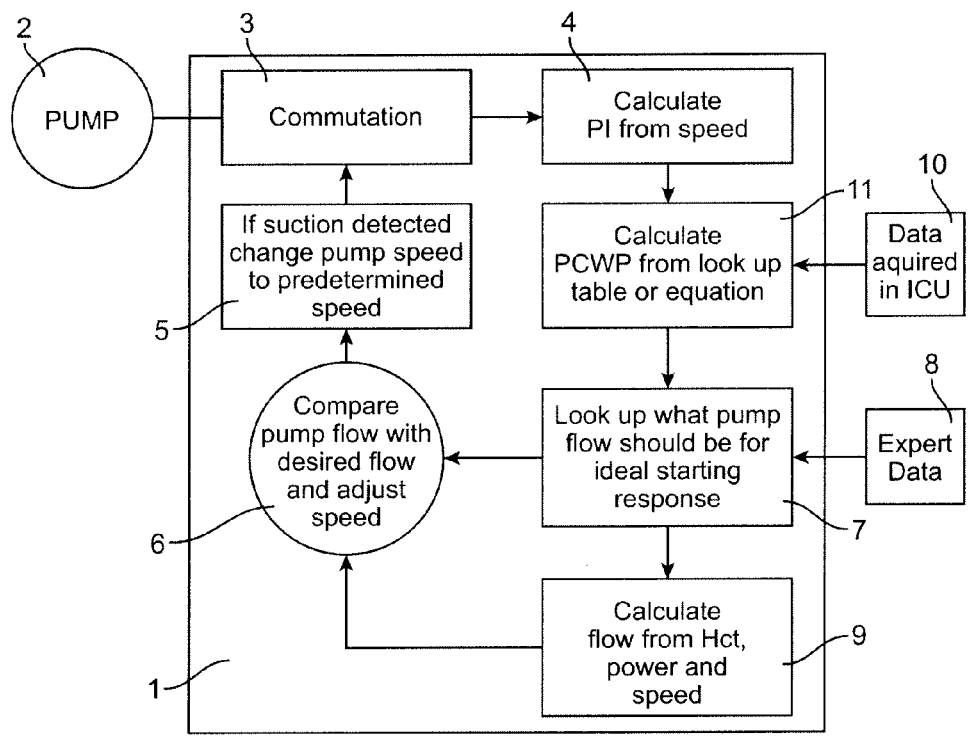
FIG. 1 depicts a schematic view of a first preferred embodiment of the present invention.

In a first preferred embodiment of the present invention, as depicted in FIG. 1, a control system 1 is used to control the target speed of a rotary blood pump 2. The rotary blood pump 2 may be implantable or extracorporeal; and may also be a left ventricle assist device. The preferred rotary blood pumps 2 for use with the first embodiment of the present invention are described in: U.S. Pat. No. 6,227,797 (Watterson et al) or U.S. Pat. No. 6,866,625 (Ayre et al) and the descriptions of these inventions are included herein.

The control system 1 may include several steps or modules to control the target speed of the rotary blood pump 2. Preferably, the control system 1 includes a commutation module 3. The commutation module 3 provides the rotary blood pump 2 with an electromagnetic drive signal to rotate a rotor or impeller (not shown) positioned within the rotary blood pump 2. The commutation module 3 also may detect the actual pumping speed or the actual speed of rotation of the impeller within the rotary blood pump 2 using back EMF detection.

The actual pumping speed may then be used by the control system 1 to derive or calculate a Pulsatility Index ("PI") and this is depicted as step 4 in FIG. 1.

The control system 1 then may also derive or calculate Pulmonary Capillary Wedge Pressure ("PCWP"), which also can be referred to as "preload", from a look-up table of set values or from an equation. This is shown in FIG. 1 as step 11. At this step 11, the control system 1 may also receive additional external input from data acquired in an Intensive Care Unit ("ICU") environment and is depicted in step 10.

Preferably, the control system 1 then calculates the most preferred pump flow rate derived or calculated from an ideal or theoretically "Starling-Like" response (see below) and this is depicted in FIG. 1 as step 7.

At step 7, the control system 1 may also receive additional expert data 8. This expert data 8 is generally data entered by an expert or medical professional and may generally include data such as haemocrit (herein referred to as "Hct") levels derived from separate blood pathology testing. If the control system 1 receives this expert data 8 at step 7, the control system 1 proceeds to step 9. Step 9 allows the control system 1 to calculate flow derived by Hct, power and pump speed.

If no expert data 8 is received by the control system at step 1, the control system 1 then proceeds to step 6. During step 6, the control system 1 compares the actual pump flow with the desired pump flow and adjusts the pump speed signal, accordingly.

Step 5 allows the control system 1 to determine whether a suction event has or is about to occur and further allows the control system 1 to reduce the pumping speed signal to avert the suction event, where necessary.

Step 3 in the control system 1 allows the control system 1 to convert the pump speed signal into a commutation signal to drive the rotation of the impeller within the rotary blood pump 2.

Figure 2:
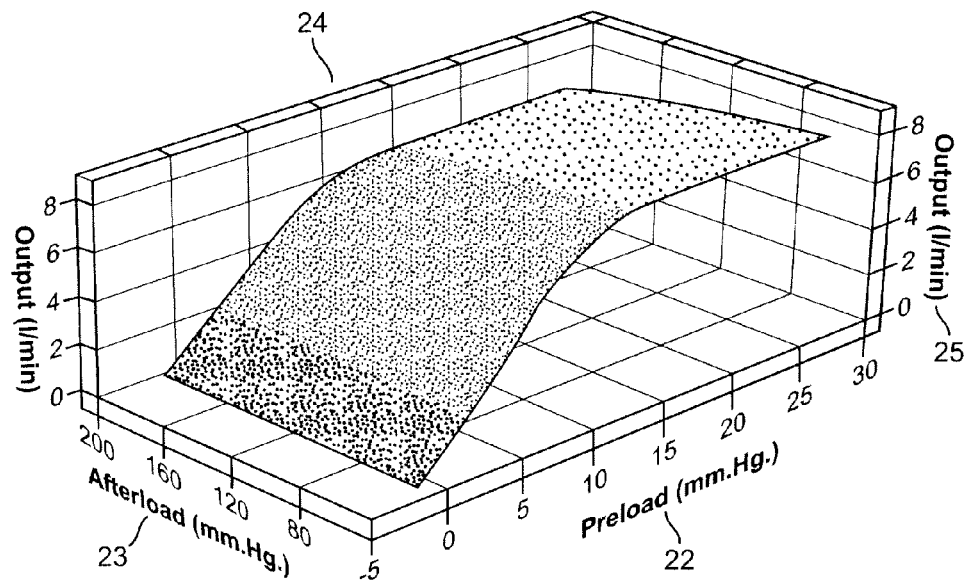
FIG. 2 depicts a graph of an example of a relatively normal starling response of the natural healthy heart.

Generally, a normal healthy heart follows the relationship depicted in the graph 24 of FIG. 2. Wherein, the output of the heart or Cardiac Output 25 (herein referred to as "CO") behaves according to the PCWP 22 for a given Mean Arterial Pressure 23 (herein referred to as "MAP" or "afterload"). This relationship is known as the "Frank-Starling Law of the heart" or "Starlings law of the heart" to persons working in this area. A relatively normal healthy heart is known to have a "Starling-like" response and may have a relatively normal range of MAP 23 of between 70 mm Hg to 120 mm Hg. There exists a close relationship of curves representing CO 25 as a function of PCWP 22. Data from patients experiencing heart failure may generate a family of curves wherein the CO 25 is reduced for a given PCWP 22.

Preferably, as depicted in FIG. 1, the control system 1 may vary the pump output or pump speed using a control algorithm. The control system 1 cooperating with the rotary blood pump 2 may actively restore the CO 25 of the heart failure patient to relatively normal levels for given PCWP 22 values.

Figure 4:
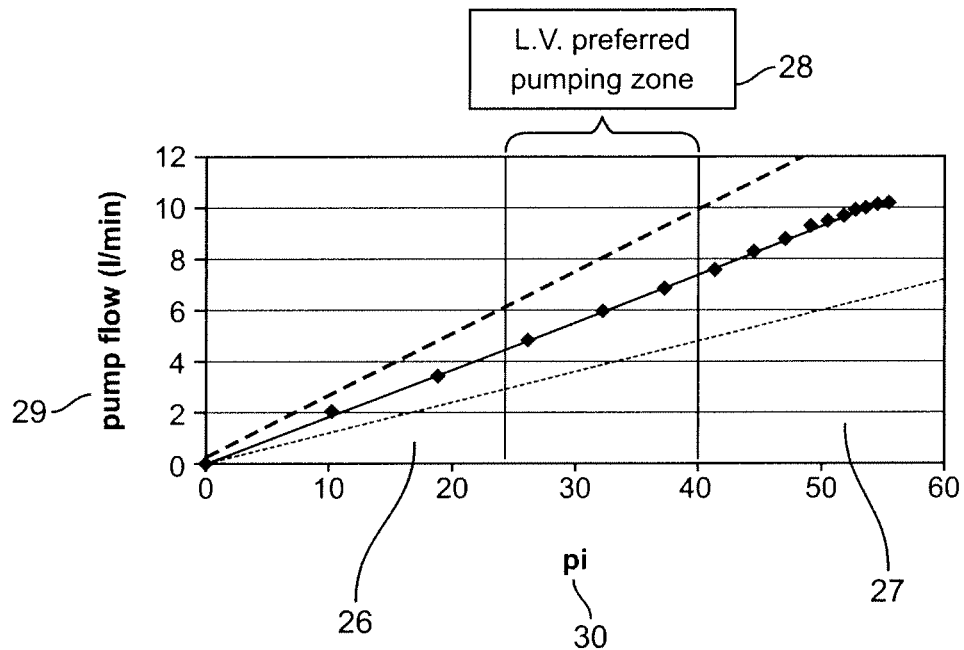
FIG. 4 depicts a graph wherein pump flow has been plotted against a Pulsatility Index (herein referred to as 'PI')

This may be non-invasively achieved by observing the pulsatility amplitude or PI 30 of pump speed and thereby allowing a relatively unique relationship between PI 30 and PCWP 22 to be able to be established for each patient. FIG. 4 depicts several examples of PI 30 being mapped against p/flow 29 (which is effectively the equivalent of blood flow through the blood pump 2). Preferably, the pump 2 is being driven at a pumping speed within the LV preferred pumping zone 28, which defines the optimal pumping conditions for the pump 2 used in this embodiment. Lower zone 26 depicts a region wherein the pumping speed is relatively too low and upper zone 27 depicts a region wherein the pumping speed is relatively too high.

Figure 5:
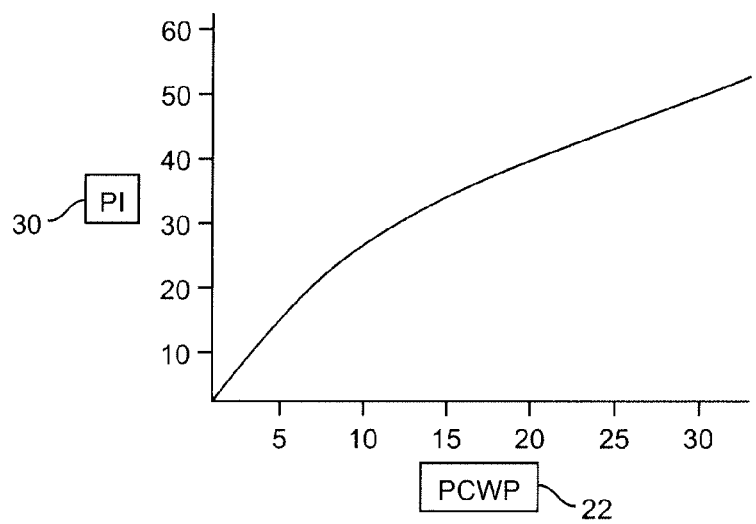
FIG. 5 depicts a graph demonstrating an example relation between PCWP to PI.

Relationships for PI 30 and PCWP 22 can be established for each patient by incrementing pump speed and recording PCWP 22 using standard measurement techniques while the patient is in intensive care. A diagram demonstrating this unique relationship is shown in FIG. 5.

Figure 6:
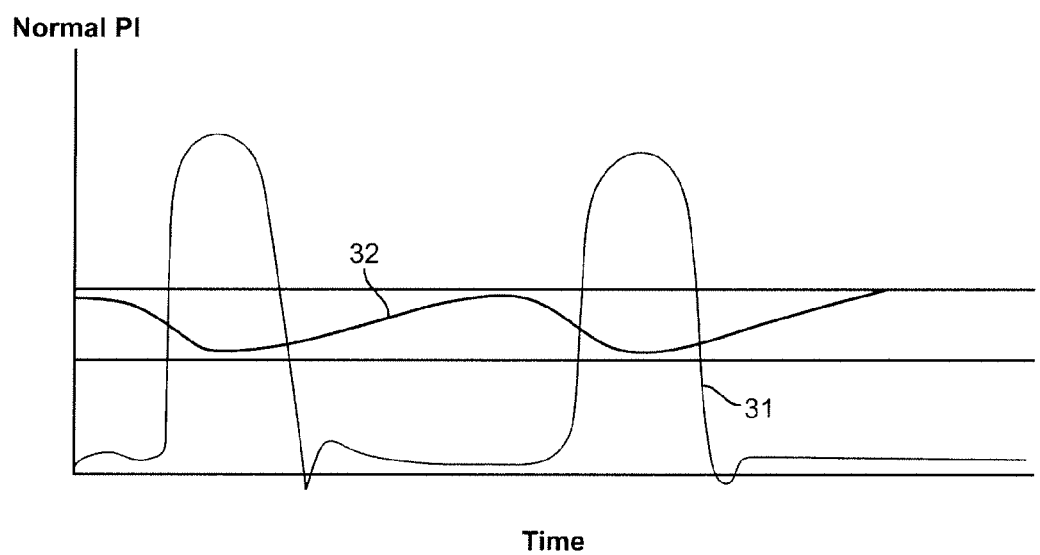
FIG. 6 depicts a graph wherein Left Ventricular Pressure (herein referred to as 'LVP') is compared to pump speed over time and further wherein PI is set at a relatively normal level.
Figure 7:
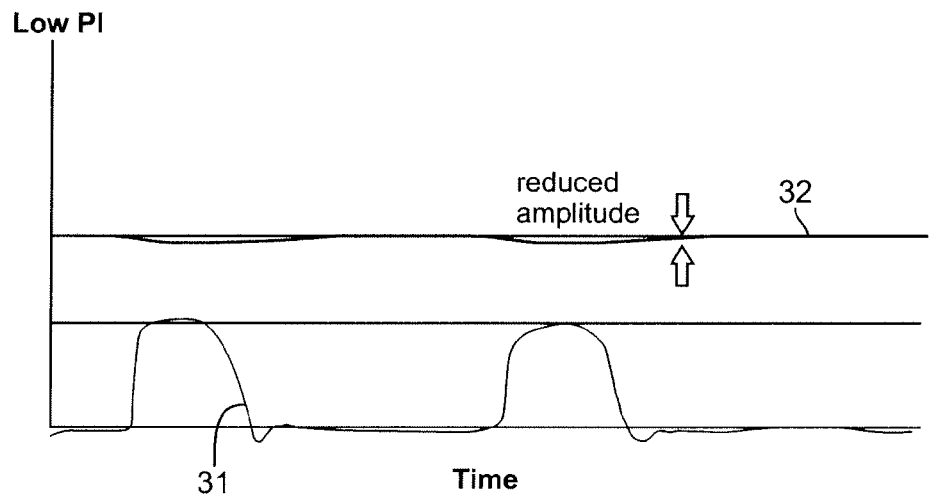
FIG. 7 depicts a similar graph to FIG. 6, wherein the PI is set at a relatively low level.

PI 30 may be derived from instantaneous speed of a rotor within the rotary blood pump 2. PI 30 may therefore be used in feedback loop in the control system 1 to produce relatively normal response curves for each patient. The pressurisation of the Left Ventricle (herein referred to as 'LV') and its influence of rotor speed is shown in FIG. 6 (normal pulsatility) and FIG. 7 (low pulsatility).

Figure 3:
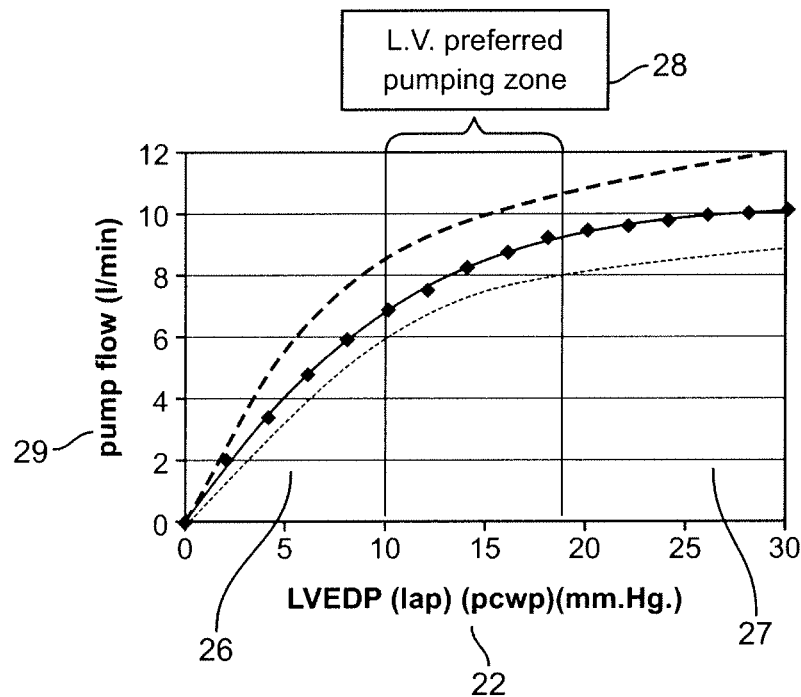
FIG. 3 depicts a graph of an example data from a theoretical healthy patient with varying the cardiac outputs compared to Pulmonary Capillary Wedge Pressure (herein referred to as 'PCWP') beyond the normal "Starling-Like" response of a typical patient.

PI 30 may be a general indication of the pulsatility of blood flowing through the rotary blood pump 2. Preferably, clinicians or patients may set a pumping speed of the rotary blood pump 2 by inputting a target speed into the control system 1. This original target speed may be interpreted by the control system 1 as either a single set point or a desired operating range for pump speed (example preferred ranges 28 in FIGS. 3 & 4). The amount of blood delivered from the LV to the pump varies across the cardiac cycle depending on several factors (including but not limited to preload, after-load, cardiac contractility, stroke volume, and heart rate). As a result, the rotor speed may vary significantly with the cardiac cycle. Preferably, PI 30 may be calculated by measuring the amplitude of these variations over one or several cardiac cycles and scaling this by a constant to produce an index between 0 and 100. Preferably, the normal range for PI 30 is set to about 20 to 45 units.

Increases in LV flow rates generally lead to increases in blood reaching or delivered to the rotary blood pump 2. As Left Ventricle Pressure 31 ('LVP') increases, aortic pressures may become relatively negative and the pressure differential across the rotary blood pump 2 may decrease. This decrease in pressure across the pump 2 may also lead to a reduction in flow within the pump 2. Increased fluid loads may cause the rotor in the pump 2 to slow slightly. When LVP 31 is reduced, the rotor within the pump 2 may slightly increase in rotation speed. Amendments to the actual pump speed 32 may alter the PI 30, as the effectiveness of ventricular unloading is altered. Additionally, when the aortic valve no longer opens (because of relative pressure or mechanical failure), PI 30 may be reduced.

Increasing the target speed may cause maximum LVP 31 to drop as the LV is unloaded more quickly and aortic flow decreased. The pump speed waveform dampens (less variation in speed across the cardiac cycle) and pulse pressure lowers and disappears.

With static system performance parameters, increasing target speed may lead to a decrease PI 30. This situation is demonstrated in the graph shown in FIG. 7.

Decreasing the target speed may allow the LV more time to fill and thus permits it to contract more effectively and leads to improved pulsatility. With a relatively static system, performance parameters set for a decreasing target speed may lead to increase PI 30.

A relatively low PI 30 may suggest that the LV is not adequately contracting and this may be a result of the pump target speed being too high. This generally results in overpumping blood 26 from the LV.

High PI 30 may generally indicate that there is increased pulsatility of flow through the pump. In situations where a high PI 30 is being experienced, pump target speed may need to be increased to more efficiently offload the ventricle. A high PI 30 may also occur where the pump target speed is too high relative to the amount of blood being delivered to the pump. The ventricle walls may collapse may lead to temporary increase in PI 30. These types of situations may be indicative of underpumping 27 of the LV.

Preferably, PI may be calculated by the following formula:

PI=(Maximum pump speed−Minimum pump speed)/ Pulsatility scaling factor

In the first embodiment of the present invention, PI 30 is calculated by the averages of the last 5 speed samples executed at 40 millisecond intervals. The preferred array stores the last 100 averaged speed samples for comparison. Instantaneous speed values 32 may be updated at a rate dependant on the pump speed (i.e. the speed samples may be collected every $8^{th}$ transition of the pump speed signal from low to high) but where the sampling preferably occurs every 40 milliseconds. PI 30 may also be detected in respect of cardiac cycles and the preferred control system may detect PI 30 over 4 cardiac cycles (assuming average rate is 60 bpm=5 secs)

For each patient a relationship is established between PI 30 and PCWP 22 initially through invasive measurement of PCWP 22. This relationship is produced between the desired CO 25 of the patient as a function of PI 30.

The most preferred rotary blood pump 2 includes a relatively flat flow rate Vs pressure curve or relationship for any given pump speed, a characteristic of centrifugal pumps but particularly with those which utilise a hydrodynamic bearing in their design. This characteristic further assists in providing a "Starling-Like" response, when used in combination with the present embodiment.

In this first preferred embodiment, the actual pump speed may be used to derive PI 30 by the control system 1. The actual pump speed signal provides a relatively low noise signal for use by the control system 1 (especially when compared to the signal of the current drawn by the motor of the pump) and actual pump speed also does not include other variables within it's signal composition (the signal generated in relation to current or power used by the motor of the pump may typically include other variables such as preload values, pressures and left atrial pressures).

A person working in this area may also appreciate that the automatic calculation of LVP 31 and PI 30 by the control system 1 may be replaced with implantable sensors (not shown). These implantable sensors may detect the input data directly and feed back this data directly to the control system 1 and may be implanted in the patient. The control system 1 may then amend the target pump speed accordingly based on these detected inputs.

The control system 1 may also provide a pulsed target speed to the rotary blood pump 2. This pulsed target speed may attempt to emulate or enhance the pulsing of the normal patient's heart. The pulsing target speed allows the rotary blood pump 2 to be continuously operated to avoid thrombogenesis. The pulsing target speed generally occurs within a range of between 1250-3000 rpm. The pulsing of target speed may also be timed with the detected heart rate of the patient. Additional heart rate sensors (not shown) may directly detect the patient's heart rate in real-time and feed this information back to the control system for timing adjustment to the pulsing target speed.

The control system 1 may also include a selective mode called 'CPR mode' (not shown), which can be selectively activated by clinicians. CPR mode may be activated by a software interface working with the control system 1 and preferably is activated when the patient requires external CPR. The control system 1, when in CPR mode, reduces the pump target speed range to between 1250-1800 rpm. The preferred target speed of the control system 1 in CPR mode is about 1250 rpm. In CPR mode, the forward flow of blood through both the pump and aortic valve is maintained and retrograde flow back into the ventricle is avoided, provided that the external CPR generates a Mean Arterial Pressure ('MAP') of at least 40 mm Hg. In CPR Mode, the rotary blood pump continues to run at a minimum speed so that the risk of thrombogenesis proximal to the rotary blood pump or patient's heart is reduced or eliminated. Preferably, this minimum speed is low enough to allow the ventricle time to fill from the left atrium, but not from the aorta via the pump conduit. This should lead to resolution of the suction event and more effective contractions during periods of haemodynamic compromise.

Additionally, if the control system 1 detects the imminence of a suction event, the control system 1 may preferably automatically activate CPR mode reducing the pump speed to a default value or a set value. The effect of the activation of the CPR mode is that the target speed of the pump is quickly reduced to a minimum safe operating speed. The minimum safe operating speed achieves all of the aforementioned advantages of CPR mode.

Figure 8:
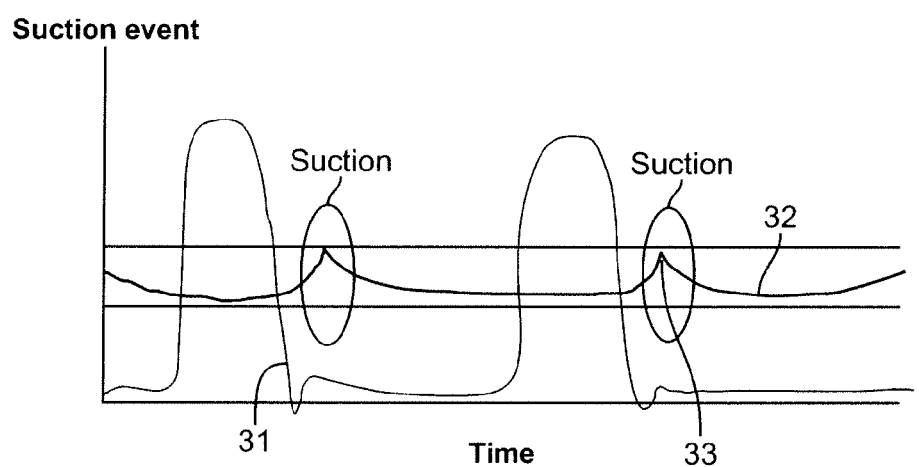
FIG. 8 depicts a similar graph to FIG. 6, wherein a suction event has occurred.

Additionally, the control system 1 may also calculate the second derivative of instantaneous speed (not shown) of the rotary blood pump 2 and then use this calculated second derivative of speed of speed to predict the imminence of a suction event. The second derivative of instantaneous speed may show sharp angular peaks 33 as shown in FIG. 8, when a suction event may be imminent. These peaks are generally the result of the LV wall being rapidly pulled towards the septal wall of the heart at the end of LV ejection. The sudden reduction in pump flow unloading the pump's rotor casing the speed to rise rapidly. This situation accentuated by low blood volume in the LV caused by low PCWP 22. Detection of these sharp angular peaks 33 also allows the detection of a suction event. The control system 1 may then reduce the target speed of the rotary blood pump 2 to remedy or at least partially avert the imminent suction event.

The above descriptions detail only some of the embodiments of the present invention. Modifications may be obvious to those skilled in the art and may be made without departing from the scope and spirit of the present invention.

The invention claimed is:

1. A control system for restoring a cardiac output of a patient using a rotary blood pump, comprising:
    a control algorithm configured to adjust a pump speed signal so as to maintain a pulsatility index for the patient at or near a predetermined value; and
    a commutation module configured to receive the adjusted pump speed signal and convert the adjusted pump speed signal into a drive signal for the pump;
    wherein the control system is configured to provide a drive signal as a pulsed target speed to emulate a normal pulsing of the patient's heart.

2. The control system of claim 1, wherein the pulsed target speed is timed according to a detected heart rate of the patient.

3. The control system of claim 2, wherein the pump is continuously operated by the control system when the pulsed target speed is used to control the pump.

4. The control system of claim 1, wherein the pulsatility index is maintained within a range of 20-45 units with respect to a range of 0 to 100 for a pulsatility index measured when the patient's heart is operating within normal levels.

5. The control system of claim 1, wherein the control system uses a measured pulsatility index of the patient to derive a preload.

6. The control system of claim 5, wherein the control algorithm is configured to maintain the preload within a predetermined range by adjusting the pump speed signal.

7. The control system of claim 1, wherein the measured pulsatility index is derived from an actual motor speed signal or a signal received from a sensor.

8. The control system of claim 7, wherein the control system is configured to mimic starling curve responses of a natural heart.

9. The control system of claim 8, wherein the control system uses preload to mimic starling curve responses of a natural heart.

10. The control system of claim 1, wherein the control system includes a selective mode that minimizes a target pump speed to achieve forward blood flow through both the pump and the patient's aortic valve, while avoiding retrograde flow.

11. The control system of claim 1, wherein the pulsatility index is proportional to the difference between minimum pump speed and maximum pump speed over a plurality of cardiac cycles and wherein the predetermined value is based on a pre-determined relationship between pulsatility index and pulmonary capillary wedge pressure (PCWP) for the patient.

12. The control system of claim 1,
wherein the control algorithm is further configured to detect a suction event based on the second derivative of the pump speed.

13. The control system of claim 12, wherein the control algorithm is configured to compute a desired pump flow from haemocrit, motor power and pump speed.

14. The control system of claim 12, wherein the control algorithm is configured to compute a desired pump flow based on an ideal starling-like response.

15. A method for restoring a cardiac output of a patient using a rotary blood pump, comprising:
adjusting a pump speed signal so as to maintain a pulsatility index for the patient at or near a predetermined value; and
converting the adjusted pump speed signal into a commutation signal;
wherein the commutation signal provides a pulsed target speed to the pump to emulate a normal pulsing of the patient's heart.

16. The method of claim 15, wherein the pulsed target speed is timed according to a detected heart rate of the patient.

17. The method of claim 15, wherein the pump is continuously operated by the control system in order to produce the pulsed target speed.

18. The method of claim 15, wherein the adjusting step further includes the step of reducing a target speed for the pump if a computed second derivative of the pump speed indicates the occurrence of a suction event.

19. The method of claim 15, further including the step of detecting the patient's heart rate and timing the pulsed target speed according to the detected heart rate.

20. The method of claim 15, wherein the signal for adjusting pump speed is based on a pulsatility index derived from an actual motor speed signal or sensor signal.

* * * * *